United States Patent
Carroll

(10) Patent No.: US 6,361,763 B1
(45) Date of Patent: Mar. 26, 2002

(54) PHOTOCHROMIC TANNING AND SUNSCREEN LOTION

(76) Inventor: George H. Carroll, 3033 Grove La., Ventura, CA (US) 93003

( * ) Notice: Subject to any disclaimer, the term of this patent is extended or adjusted under 35 U.S.C. 154(b) by 0 days.

(21) Appl. No.: 09/535,179

(22) Filed: Mar. 27, 2000

(51) Int. Cl.[7] .............................. A61K 7/42; A61K 7/44; A61K 7/00
(52) U.S. Cl. .............................. 424/59; 424/60; 424/401
(58) Field of Search .............................. 424/401, 59, 60

(56) References Cited

U.S. PATENT DOCUMENTS

| | | | | |
|---|---|---|---|---|
| 4,134,853 A | * | 1/1979 | Ehrlich et al. | 252/300 |
| 5,017,225 A | * | 5/1991 | Nakanishi et al. | 106/21 |
| 5,166,345 A | * | 11/1992 | Akashi et al. | 544/71 |
| 5,176,905 A | * | 1/1993 | Ohno et al. | 424/69 |
| 5,208,132 A | * | 5/1993 | Kamada et al. | 430/138 |
| 5,581,090 A | * | 12/1996 | Goudjil | 250/474.1 |
| 5,628,934 A | * | 5/1997 | Ohno et al. | 252/586 |
| 5,730,961 A | * | 3/1998 | Goudjil | 424/61 |
| 5,762,915 A | * | 6/1998 | Saito et al. | 424/59 |
| 6,080,415 A | * | 6/2000 | Simon | 424/401 |
| 6,123,952 A | * | 9/2000 | Lagrange | 424/401 |

FOREIGN PATENT DOCUMENTS

| | | | |
|---|---|---|---|
| FR | 1 604 929 A | * | 6/1972 |
| JP | 356049312 A | * | 5/1981 |
| JP | 361275209 A | * | 12/1986 |
| JP | 04139109 A | * | 5/1992 |
| JP | 409100469 A | * | 4/1997 |

* cited by examiner

Primary Examiner—Jose' G. Dees
Assistant Examiner—Marina Lamm
(74) Attorney, Agent, or Firm—Dennis H. Lambert

(57) ABSTRACT

A photochromic tanning and sunscreen lotion having photochromic compounds that change color upon exposure to sunlight or other sources of ultraviolet radiation (UV) to create the appearance of a tanned skin, and which also form a shield against UV radiation to thereby provide an effective sunscreen.

12 Claims, No Drawings

PHOTOCHROMIC TANNING AND SUNSCREEN LOTION

BACKGROUND OF THE INVENTION

1. Field of the Invention

This invention relates generally to sunscreen and tanning lotions. More particularly, this invention relates to a lotion that is applied to the skin and which contains photochromic compounds that react upon exposure to ultraviolet radiation, e.g. sunlight, to produce a color change, simulating a suntan, and which also react to provide protection against ultraviolet radiation, thus producing a synergistic effect.

2. Prior Art

Because of work-related and/or recreational activities, most people spend at least some portion of their lives outdoors and are therefore exposed to sunlight. exposure to sunlight, and more specifically, exposure to the UV rays in sunlight, creates free radicals that ultimately break down the protein network in the skin. In mild cases this leads to photo-aging and wrinkling of the skin, and in more severe cases can lead to the growth of cancerous cells (melanoma).

In spite of these hazards, which are generally known, many people seek exposure to sunlight, or to the UV lamps in a tanning salon, in order to obtain a tan. In fact, many people use the services of a tanning salon so that they can obtain a tan prior to visiting a public pool or beach.

Whether they are going to be exposed to natural sunlight or to the UV lamps in a tanning salon, most people apply some type of skin protection, e.g., tanning lotions and/or sunscreens, in order to avoid becoming burned and to minimize the risks associated with exposure to UV radiation.

Sunscreens are formulated with UV inhibitors or absorbers to block or reduce the amount of UV rays reaching the skin, thereby reducing or eliminating the potential damage caused by exposure to UV radiation. Approved sunscreen actives include aminobenzenic acid, avobenzone, cinoxate, dioxybenzone, homosalate, menthyl anthranilate, octocrylene, octyl methoxycinnamate, octyl salicylate, oxybenzone, padimate, phenylbenzinadazole sulfonic acid, sulisbenzone, trolamine salicylate and zinc oxide. Two or more of these active ingredients may be combined with other materials to produce a cream, lotion or spray lotion with an appropriate sun protection factor (SPF) and broad spectrum sun protection and that is chemical- and photo-stable is water resistant and has reduced skin penetration. Suspoemulsions can also be used to insure that the most protection is obtained from selected sunscreen combinations, e.g., to combine amphophilic microfine titanium dioxide with organic sunscreens using relatively small amounts of sunscreen actives.

Persons venturing to the pool or beach for at least the first few times following a season indoors may be self-conscious about their lack of a tan, and are therefore anxious to obtain a tan as quickly as possible. However, if these persons are applying a sunscreen as protection from the harmful effects of UV radiation, they are also delaying the tanning process since the very benefits conferred by the sunscreens also tend to impede tanning of the skin. Consequently, many people forego the benefits of a sunscreen in favor of more quickly obtaining a tan.

At least partially in response to these problems, the cosmetics industry has developed products that alter the tone or color of the skin in order to produce an artificial tan. However, these artificial tanning products do not provide the protection imparted by a sunscreen, nor do the artificial tans obtained by their use appear the same as a tan obtained from exposure to sunlight or to the UV lamps in a tanning salon. Further, use of these products may lead to a false sense of security since the person's skin remains unprotected against the harmful effects of UV radiation even though it appears tan, and the person's skin can become burned if exposed for even a short period of time to sunlight or to the UV lamps in a tanning salon.

Accordingly, there is need for a tanning lotion and sunscreen that effectively protects the skin from the harmful effects of UV radiation, but which at the same time confers the appearance of a tan as soon as exposed to UV radiation, whereby a person can cosmetically appear as though already tanned while seeking a tan, and at the same time be protected against the harmful effects of exposure to UV radiation.

SUMMARY OF THE INVENTION

The invention provides a tanning lotion and sunscreen that effectively protects the skin from the harmful effects of UV radiation, but which at the same time confers the appearance of a tan as soon as exposed to UV radiation, whereby a person can cosmetically appear as though already tanned at the same time he or she is seeking a tan.

More particularly, the invention comprises a tanning lotion or sunscreen formulation having photochromic compounds that change color upon exposure to sunlight or other sources of ultraviolet radiation (UV) to create the appearance of a tanned skin. As part of the color changing process, the molecules of the photochromic compounds open up and provide a UV blocking effect. Thus, the photochromic compounds produce a synergistic effect in the tanning lotion of the invention. That is, the lotion reacts to UV radiation to change color, and also blocks UV radiation.

The photochromic compounds may be mixed in a carrier that can be added to the normal formulation of a skin lotion. If desired, an additional UV absorber can be provided in these formulations which also may include a pigment and an emollient. In order to get the most protection out of sunscreen combinations, the formulator can use suspoemulsions to combine amphiphilic microfine titanium dioxide with organic sunscreens using relatively small amounts of sunscreen actives. One or more sunscreen actives may be selected from the following: aminobenzenic acid, avobenzone, cinoxate, dioxybenzone, homosalate, menthyl anthronilate, octocrylene, octyl methoxycinnamate, octyl salicylate, oxybenzone, padimate, phenylbenzinadazole sulfonic acid, sulisbenzone, trolamine salicylate and zinc oxide. This technology makes it possible to develop creams, lotions and spray lotions with high SPF and broad-spectrum sun protection.

To make suspoemulsions, titanium dioxide is added to the oil phase. Emolients with medium polarity are preferred so that a desired viscosity can be maintained in a narrow range over a wide concentration range of titanium dioxide. The formulation can be thickened by using Polyquat 37 and propylene glycol.

Examples of suitable photochromic compounds are described in U.S. Pat. Nos. 5,581,090 and 5,730,961, the disclosures of which are incorporated in full herein by reference. As noted in the '090 and '961 patents, photochromic substances are known in the art for their utilization in optics as storage media or as a means to detect UV, such as, e.g., the photochromic ultraviolet detector disclosed in the '090 patent. Among the large family of photochromic compounds are the spiropyrans and spiroxazines groups of molecules. These molecules are known for their property of changing from clear to a variety of colors and shades. Normally appearing as colorless, these spiro-compounds undergo a photochemical transformation to intensely colored form when exposed to UV. The '961 patent, in particular, discloses a material which remains clear until exposed to UV and which then exhibits color and thus becomes visible. The active chemical disclosed in the '961 patent is identified as a photochromic substance such as spiropyrans or spiroxazines molecules.

U.S. Pat. No. 5,166,345 describes a photochromic compound which exhibits high color density, is stable against heat and solvent, and which has a great repeating durability in coloring-decoloring cycles. For improved performance, the photochromic compound used to impart the appearance of a tan in accordance with the present invention can be formulated using the teachings of this patent, the disclosure of which is incorporated in full herein, whereby the stability, durability and color intensity, for example, of the compound are optimized.

Further, the composition used to make the photochromic tanning lotion of the invention may be formulated so that it is operative to change color only after exposure to UV radiation for a predetermined period of time, e.g., a few minutes. Preferably, the photochromic compounds are selected so that the color of the tanning lotion composition changes gradually upon exposure to UV, becoming increasingly darker over a period of time when exposed to UV to thereby more accurately reflect a natural tanning process.

Additionally, the tanning lotion of the invention may be formulated so that the photochromic compounds return to colorless a predetermined time after the photochromic composition is no longer exposed to UV, whereby the natural tan obtained upon exposure to sunlight or UV lamps in a tanning salon gradually replaces the artificial tan obtained by use of the formulation of the invention.

DETAILED DESCRIPTION OF THE PREFERRED EMBODIMENTS

The tanning lotion of the present invention may be colorless or it may be pigmented with a desired color. Upon exposure to sunlight or other source of ultraviolet radiation, the photochromic compounds undergo a photochemical change from clear or colorless to colored, thereby producing the appearance of a tan. At the same time, the molecules in the photochromic compounds open up to form a "shield" and protect the skin from the harmful effects of UV. In addition, sunscreen actives can be included in the formulation, if desired, although care will need to be exercised to insure that the sunscreen actives do not entirely block the UV radiation from the photochromic compounds, thereby preventing them from changing color. Some blockage or screening may be acceptable to achieve a more gradual color change, for example.

Thus, the lotion of the invention enables a person to have the appearance of a tan, while at the same time protecting him or her from the harmful effects of exposure to UV. Upon return indoors, or away from exposure to UV, the "tan" gradually fades as the photochromic compounds undergo a photochemical change to their colorless state. The time required for this fading to occur can be manipulated by appropriate design of the formulation, whereby after removal from exposure to UV, the "tan" can last for several minutes or several days, as desired. Similarly, the formulation can be designed so that the photochromic compounds react immediately upon exposure to UV, or so that they react only after elapse of a predetermined time, or so that a series of sequential reaction times are obtained so that the appearance of color is gradual and mimics the natural tanning process.

By appropriate selection of the SPF in the lotion, some exposure to UV may be permitted so that the skin gradually tans. After a desired tan has been obtained, a lotion containing maximum SPF may be applied to eliminate further exposure to UV.

To produce the lotion of the invention, a photochromic compound is mixed with any skin cream, sunscreen, moisturizing lotion, or other composition, e.g., water and mineral oil, to produce a cream, lotion or spray lotion, as desired, having suitable photostability and photoprotection.

The photochromic compound is preferably selected from the spiropyrans and spiroxazine groups of the photochromic family of compounds, such as those disclosed in U.S. Pat. No. 5,581,090, for example. The spiropyrans and spiroxazine compounds normally appear as colorless but undergo photochemical transformation and exhibit intense colors when exposed to UV radiation. By appropriate selection of these compounds, various "tan" colorations can be obtained.

The spiropyrans or spiroxazine compounds may be added to the formulation in a proportion of about 0.1 to about 1.0 percent by weight. Higher concentrations yield more intense colors. Different color hues are obtained by mixing two or more spiropyrans or spiroxazine compounds in the carrier, as necessary or desired.

The photochromic compounds may be microencapsulated in accordance with conventional techniques so that they are not subject to the action of UV until they have been exposed by the action of rubbing the lotion onto the skin, whereby they may undergo photochemical transformation only after being applied for use.

A commercially available stabilizer, such as Tinuvin 765 or Tinuvin 144 Hindred Amine by Cibra-Geigy Corporation of New York, light stabilizers of polymers, may be added to the composition to reduce oxidation processes and thereby extend the useful life of the photochromic compound. Tinuvin 765 and Tinuvin 144 Hindred Amine Light Stabilizers, available from the Additive Division of Ciba Geigy. The stabilizers may be added in a proportion of from about 2.5% up to about 3.0% by weight.

Conventional sunscreen formulations which may be used in the invention include a UV absorber or blocker, and may include a pigment and an emollient. In order to get the most protection out of sunscreen combinations, the formulator can use suspoemulsions to combine amphiphilic microfine titanium dioxide with organic sunscreens using relatively small amounts of sunscreen actives. One or more sunscreen actives may be selected from the following: aminobenzenic acid, avobenzone, cinoxate, dioxybenzone, homosalate, menthyl anthronilate, octocrylene, octyl methoxycinnamate, octyl salicylate, oxybenzone, padimate, phenylbenzinadazole sulfonic acid, sulisbenzone, trolamine salicylate and zinc oxide.

Emolients with medium polarity are preferred so that a desired viscosity can be maintained in a narrow range over a wide concentration range of titanium dioxide. The formulation can be thickened by using Polyquat 37 and propylene glycol.

The use of photochromic compounds in a tanning lotion has a synergistic effect, i.e., it is believed that when the photochromic compound molecules open up on exposure to UV rays, they will have a blocking effect on the UV rays in addition to changing color.

While particular embodiments of the invention have been illustrated and described in detail herein, it should be understood that various changes and modifications may be made to the invention without departing from the spirit and intent of the invention as defined by the scope of the appended claims.

What is claimed is:

1. A photochromic tanning lotion for application to the skin of a person to protect the skin from the harmful effects of ultraviolet radiation, and to temporarily impart a color simulating a natural tan, comprising:

one or more photochromic compounds mixed in an appropriate amount in the lotion for application to the skin, said photochromic compound undergoing a photochemical transformation from colorless to the color of naturally tanned skin when exposed to ultraviolet radiation, and also forming a UV block, to thereby produce the appearance of a natural tan upon exposure to ultraviolet radiation while at the same time protecting the user from UV radiation.

2. A photochromic tanning lotion as claimed in claim 1, wherein:

the photochromic compounds are micro-encapsulated to prevent exposure of the compounds to ultraviolet radiation until they are rubbed onto the skin of a person, whereupon the micro-encapsulation is breached so that the compounds are exposed and are subject to ultraviolet radiation.

3. A photochromic tanning lotion as claimed in claim 2, wherein:

the photochromic compounds are selected from the group consisting of spiropyrans and spiroxazine photochromic family of compounds.

4. A photochromic tanning lotion as claimed in claim 3, wherein:

the spiropyrans or spiroxazine compounds are added to the formulation in a proportion of about 0.1 to about 1.0 percent by weight.

5. A photochromic tanning lotion as claimed in claim 4, wherein:

two or more spiropyrans or spiroxazine compounds are mixed in the lotion to obtain different color hues.

6. A photochromic tanning lotion as claimed in claim 5, wherein:

a stabilizer is added to the composition to reduce oxidation processes and thereby extend the useful life of the photochromic compound.

7. A photochromic tanning lotion as claimed in claim 6, wherein:

the stabilizer is a light stabilizer of polymers.

8. A photochromic tanning lotion as claimed in claim 1, wherein:

two or more photochromic compounds are mixed in the lotion to obtain different color hues.

9. A photochromic tanning lotion as claimed in claim 1, wherein:

a stabilizer is added to the composition to reduce oxidation processes and thereby extend the useful life of the photochromic compound.

10. A photochromic tanning lotion as claimed in claim 1, wherein:

the photochromic compounds are added to the formulation in a proportion of about 0.1 to about 1.0 percent by weight.

11. A photochromic tanning lotion as claimed in claim 1 wherein:

at least one sunscreen active is in the lotion in an appropriate amount to absorb and/or block ultraviolet rays to protect the skin of the person to whom the lotion has been applied from the harmful effects of ultraviolet radiation.

12. A photochromic tanning lotion as claimed in claim 11, wherein:

the sunscreen actives are selected from the group consisting of aminobenzenic acid, avobenzone, cinoxate, dioxybenzone, homosalate, menthyl anthronilate, octocrylene, octyl methoxycinnamate, octyl salicylate, oxybenzone, padimate, phenylbenzinadazole sulfonic acid, sulisbenzone, trolamine salicylate and zinc oxide.

* * * * *